(12) United States Patent
Fu

(10) Patent No.: US 11,141,544 B2
(45) Date of Patent: Oct. 12, 2021

(54) SUBCUTANEOUS NEEDLE

(71) Applicant: Nanjing FSN Medical Co., Ltd., Jiangsu (CN)

(72) Inventor: Zhonghua Fu, Jiangsu (CN)

(73) Assignee: NANJING FSN MEDICAL CO., LTD., Jiangsu (CN)

( * ) Notice: Subject to any disclaimer, the term of this patent is extended or adjusted under 35 U.S.C. 154(b) by 145 days.

(21) Appl. No.: 15/578,834

(22) PCT Filed: Feb. 18, 2016

(86) PCT No.: PCT/CN2016/073994
§ 371 (c)(1),
(2) Date: Dec. 1, 2017

(87) PCT Pub. No.: WO2016/192415
PCT Pub. Date: Dec. 8, 2016

(65) Prior Publication Data
US 2018/0169348 A1 Jun. 21, 2018

(30) Foreign Application Priority Data
Jun. 2, 2015 (CN) .......................... 201510295202.8

(51) Int. Cl.
*A61M 5/32* (2006.01)
*A61H 39/08* (2006.01)
*A61B 17/00* (2006.01)

(52) U.S. Cl.
CPC ........... *A61M 5/3216* (2013.01); *A61B 17/00* (2013.01); *A61H 39/08* (2013.01); *A61H 39/086* (2013.01);
(Continued)

(58) Field of Classification Search
CPC ...... A61M 25/06–0656; A61M 5/3216; A61M 5/3243; A61M 2005/325; A61B 17/00; A61H 39/08; A61H 39/086
See application file for complete search history.

(56) References Cited

U.S. PATENT DOCUMENTS 3,584,625 A * 6/1971 Swick ................. A61M 25/065
604/161
3,595,230 A * 7/1971 Suyeoka ........... A61M 25/0612
604/192
(Continued)

FOREIGN PATENT DOCUMENTS

CN      201033084 Y    3/2008
CN      101390808 A    3/2009
(Continued)

*Primary Examiner* — Bradley J Osinski
(74) *Attorney, Agent, or Firm* — Muncy, Geissler, Olds and Lowe, P.C.

(57) ABSTRACT

The present invention relates to a type of medical instrument, in particular a fifth generation FSN needle, being a special tool for Fu's subcutaneous needling (FSN), comprising a needle handle, a needle core, a soft casing pipe and its handle, and a protective sleeve. The needle core is fixed on top part of the needle handle and consists of a needle core body and a needle core tip. On top part of the needle handle, a round-hole-type groove is provided. On this groove, a positioning notch is provided, including first longitudinal position point, and inlet and second longitudinal position point at two sides of the first longitudinal position point. The soft casing pipe handle is a round tube that can be inserted into said groove. On the soft casing pipe handle, a first bulge and second bulges are provided: the first bulge is used to fix the soft casing pipe and its handle; the second bulges are used to prompt sweep position.

4 Claims, 3 Drawing Sheets

(52) U.S. Cl.
CPC ... *A61M 5/3243* (2013.01); *A61H 2201/0173* (2013.01); *A61M 2005/325* (2013.01)

(56) References Cited

U.S. PATENT DOCUMENTS

| | | | |
|---|---|---|---|
| 6,379,337 B1 * | 4/2002 | Mohammad | A61M 5/322 604/162 |
| 2003/0125677 A1 | 7/2003 | Swenson et al. | |

FOREIGN PATENT DOCUMENTS

| | | |
|---|---|---|
| CN | 202740389 U | 2/2013 |
| CN | 103099732 A | 5/2013 |
| CN | 204932248 U | 1/2016 |

\* cited by examiner

SUBCUTANEOUS NEEDLE

TECHNICAL FIELD

The present invention relates to a type of medical instrument, in particular a type of FSN needle that is safer and easier to use.

BACKGROUND OF THE INVENTION

FSN has broken through traditional theory of acupuncture and had been invented by this inventor in 1996.

FSN mainly adopts made-to-order FSN needle as its tool. Based on local disease, this needle mainly enters superficial fascia. Needle stay time is 4-5 h and the needle only extends into subcutaneous loose connective tissue, not muscle layer. This new therapy can be used for some commonly seen limitative ailments and symptoms of illness at various parts of the body.

One type of existing FSN needle (application No. 201220307856.X) is actually a type of retention needle, comprising metal needle core on the needle handle, metal hollow conduit matching this metal needle core, and soft casing pipe matching this conduit. The structure is complicated and the process cost is high. Also, installation is not easy and cannot realize fixing right after withdrawal of needle core back into the soft casing pipe. In another type of FSN needle (application No. 200810155285.0), one longitudinal guide groove and one transverse snap groove that crosses it are provided on the hollow conduit, and one positioning bulge is provided on the hollow handle of the soft casing pipe. This hollow handle matches the hollow conduit and its movement trajectory in the hollow conduit is determined by the positioning bulge, the longitudinal guide groove, and the transverse snap groove. Since in actual operation, FSN requires sweeping movent in subcutaneous layer (scope of sweep is a sector area). To prevent the needle core from scuffing subcutaneous tissue, this core shall remain inside the soft casing pipe. Also, excessive withdrawal of the needle core may easily cause tearing, failing the protection, damaging the soft casing pipe, and possibly breaking this sleeve. In addition, such transverse snap groove may easily cause sliding of the soft casing pipe, resulting in disengagement of the soft casing pipe from the needle core or unnecessary leakage to outside via the needle core during operation.

Besides, since the FSN needle is relatively small and near skin during treatment, operation space is relatively small and it is difficult to accurately change position of soft casing pipe and its handle, bringing difficulty and even additional pain of patient during treatment. Therefore, this type of FSN needle requires improvement.

SUMMARY OF THE INVENTION

For problems in the existing technique, this invention proposes fifth generation FSN needle. Via design of positioning notch, soft casing pipe, and soft casing pipe handle, these problems have been overcome, with good effect. The technical scheme is described below.

A fifth generation FSN needle, comprising a steel needle handle, a needle core, a soft casing pipe and its handle, and a protective sleeve; wherein:

the needle core is fixed on top part of the steel needle handle and consists of a needle core body and a needle core tip;

a round-hole-type groove is provided on top part of the steel needle handle and on this groove, a positioning notch is provided, including first longitudinal position point, and inlet and second longitudinal position point at two sides of the first longitudinal position point;

the soft casing pipe handle is a round tube that can be inserted into said groove and a first bulge is provided on the soft casing pipe handle, coinciding with shape of said first position point and second position point; on the fixing part extending from the round-hole-type groove, two symmetric second bulges are provided and adopt strip shape as a preference;

when the first bulge is at first position point, the needle core tip extends from the soft casing pipe;

when the first bulge is at second position point, the needle core tip is partially or fully hidden in the soft casing pipe (hidden in the soft casing pipe as a preference);

anti-slip points are provided on the face of the steel needle handle consistent with the first bulge, position of the face with anti-slip points is consistent with position of the groove, and both this face and its opposite face are concave, to facilitate holding by hand and exerting force.

Beneficial effects of this invention are as follows: 1. solving the problem of easy pulling-out of the needle by carelessness; 2. solving the problem of difficult fixing of soft casing pipe and its handle after moving between position points; 3. increased degree of identification for the sweeping movement, hence improved accuracy.

DESCRIPTION OF DRAWING FIGURES

Figure 1:
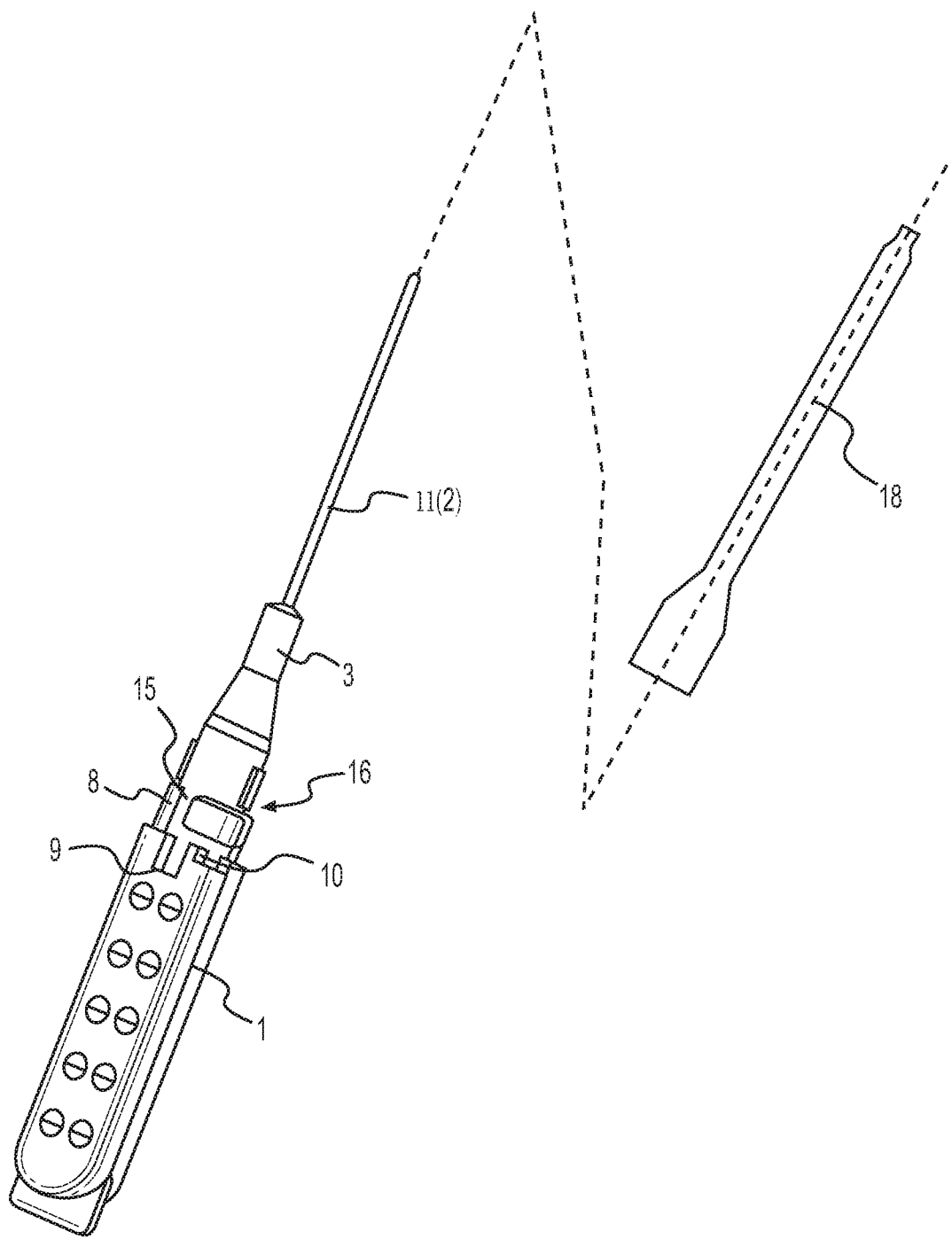
FIG. 1 is a schematic of overall structure of preferred embodiment of this invention.

In these figures: 1—steel needle handle, 2—needle core, 3—soft casing pipe and its handle, 6—positioning notch, 7—anti-slip points, 8—inlet, 9—first position point, 10—second position point, 11—soft casing pipe, 12—soft casing pipe handle, 13—first bulge, 14—second bulge

PREFERRED EMBODIMENT

The following describes this invention in details in combination with the drawing figures and a preferred embodiment.

Figure 2:
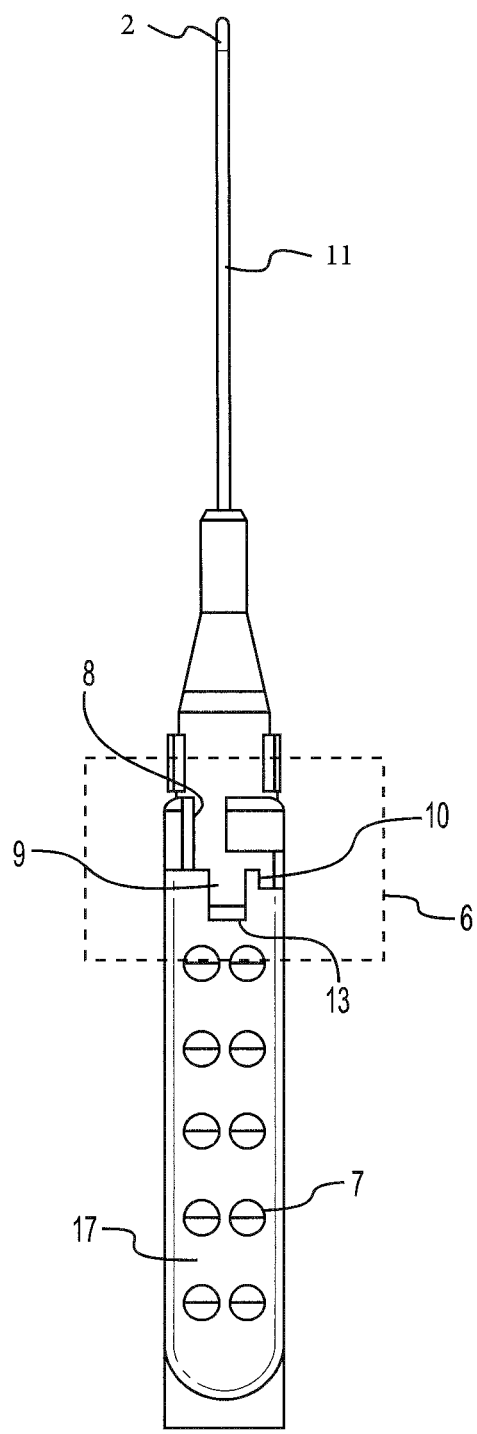
FIG. 2 is a front view of preferred embodiment of this invention.
Figure 3:
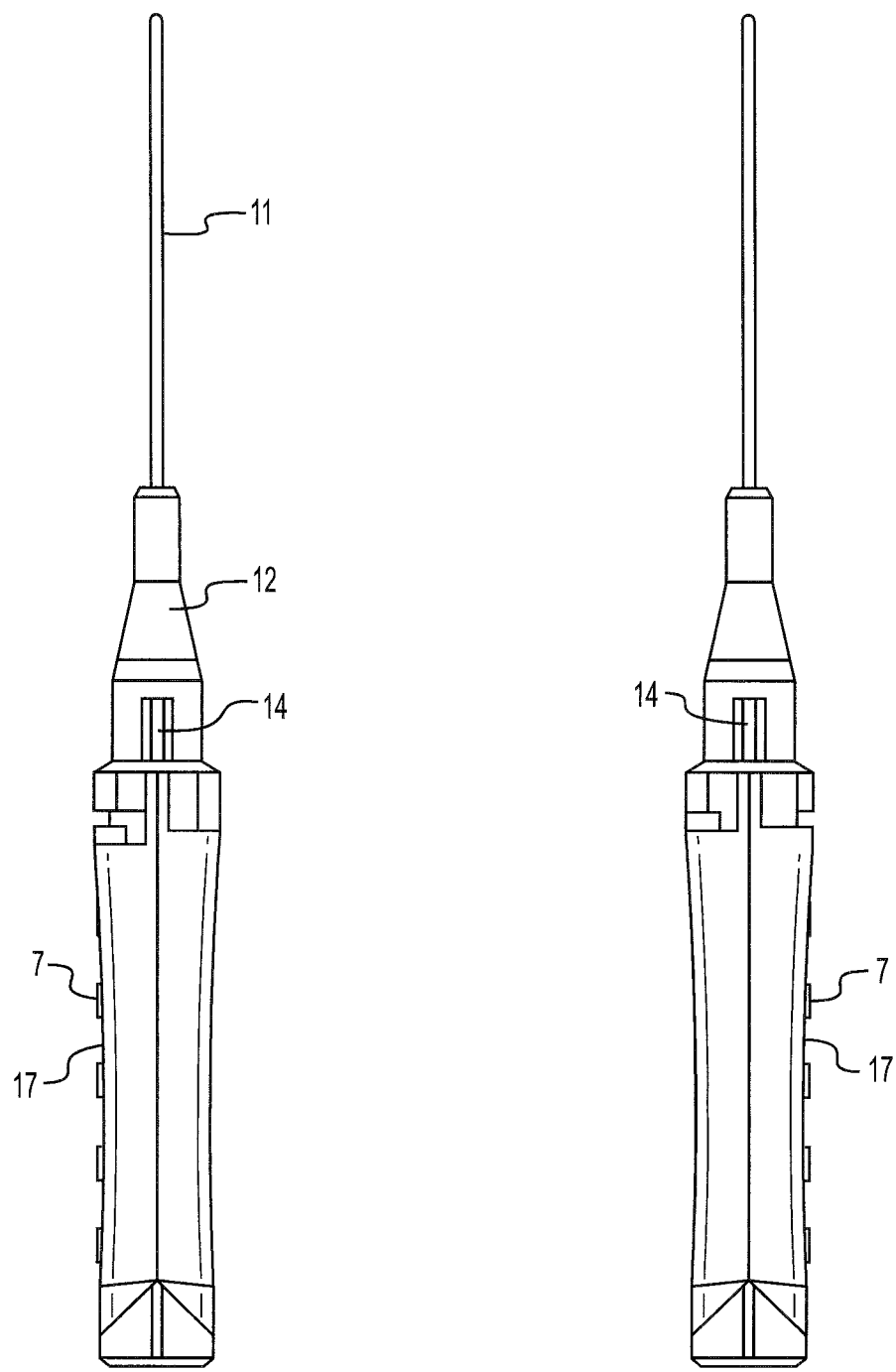
FIG. 3 shows a left view and a right view of preferred embodiment of this invention.

A fifth generation FSN needle shown in FIG. 1-3, comprising a steel needle handle 1, a needle core 2, a soft casing pipe and its handle 3, and a protective sleeve, wherein:

the needle core 2 is fixed on top part of the steel needle handle 1 and consists of a needle core body and a needle core tip;

on top part of the steel needle handle 1, a round-hole-type groove is provided, and on this groove, a positioning notch 6 is provided, including first longitudinal position point 9, and inlet 8 and second longitudinal position point 10 at two sides of the first longitudinal position point 9;

width of the part connecting second position point 10 with first position point 9 is equivalent to width of first bulge 13;

soft casing pipe and its handle 3 includes soft casing pipe 11 and soft casing pipe handle 12, with soft casing pipe handle 12 being a round tube that can be inserted into the round-hole-type groove;

on soft casing pipe handle 12, first bulge 13 is provided and coincides with shape of first position point 9 and second position point 10;

two second bulges 14 are symmetrically provided on soft casing pipe handle 12 extending from the round-hole-type groove.

As a preference, first bulge 13 has the shape of transverse strip and second bulge 14 has the shape of longitudinal strip.

First, first bulge 13 is at first position point 9. At this time, the needle core tip extends out of soft casing pipe and its handle 3. Pierce FSN needle into skin, and then pull steel needle handle 1 and rotate soft casing pipe and its handle 3, to place first bulge in second position point 10 and hide needle core tip in soft casing pipe and its handle 3.

Anti-slip points 7 are provided on the face of the steel needle handle 1 consistent with the bevel face, and both this face and its opposite face are concave, to facilitate holding by hand and exerting force.

This preferred embodiment is only a good example of this invention and not intended to limit this invention. Any modification, equivalent replacement, or improvement within the concept and principle of this invention shall be included in the scope of protection of this invention.

The invention claimed is:

1. A subcutaneous needle, comprising a steel needle handle, a needle core, a soft casing pipe and its handle, and a protective sleeve; wherein:

said needle core is fixed on a top part of said needle handle and includes a needle core body and a needle core tip, wherein the needle handle and the needle core are coupled along a longitudinal axis;

a circumferential groove is provided on the top part of said needle handle and surrounds and extends along the longitudinal axis of the needle handle to position the soft casing pipe and its handle, and the top part of said needle handle penetrates through the circumferential groove along the longitudinal axis and further includes a positioning notch connecting to the circumferential groove and including a first longitudinal position point, an inlet extending along the longitudinal axis of the needle handle and a second longitudinal position point, wherein the inlet, the first longitudinal position point and the second longitudinal position point are arranged in a latitudinal distribution surrounding the longitudinal axis, wherein the inlet and the second longitudinal position point are respectively located at two sides of the first longitudinal position point according to the longitudinal axis, and wherein the first longitudinal position point and the second longitudinal position point are directly connected to the inlet, wherein the first longitudinal position point and the second longitudinal position point overlap with each other in the latitudinal distribution;

said soft casing pipe handle is a round tube that is accommodated by the circumferential groove and a first bulge is provided on a circumferential surface of an end of said soft casing pipe handle;

when said first bulge is at said first longitudinal position point, said needle core tip extends from said soft casing pipe;

when said first bulge is at said second longitudinal position point, said needle core tip is partially or fully hidden in said soft casing pipe.

2. The subcutaneous needle of claim 1, wherein said first bulge coincides with a shape of said first longitudinal position point and with a shape of said second longitudinal position point.

3. The subcutaneous needle of claim 1, wherein a second bulge is provided on said soft casing pipe handle.

4. The subcutaneous needle of claim 1, wherein anti-slip points are provided on at least one surface of said steel needle handle.

* * * * *